United States Patent [19]
Miller

[11] Patent Number: 6,150,166
[45] Date of Patent: *Nov. 21, 2000

[54] SYSTEM FOR PROPAGATING IN VITRO TISSUE CULTURES OF A PLANT SPECIES

[75] Inventor: Virginia I. Miller, Lincoln, Nebr.

[73] Assignee: Board of Regents of University of Nebraska, Lincoln, Nebr.

[*] Notice: This patent issued on a continued prosecution application filed under 37 CFR 1.53(d), and is subject to the twenty year patent term provisions of 35 U.S.C. 154(a)(2).

[21] Appl. No.: 09/033,360

[22] Filed: Mar. 2, 1998

[51] Int. Cl.$^7$ ....................................................... C12N 5/02
[52] U.S. Cl. ......................... 435/420; 435/410; 435/430; 435/430.1; 435/431; 435/283.1; 47/58.1
[58] Field of Search ..................................... 435/410, 420, 435/430, 430.1, 431, 283.1; 47/58.1

[56] References Cited

U.S. PATENT DOCUMENTS

| | | |
|---|---|---|
| 4,860,490 | 8/1989 | Morris et al. . |
| 5,287,652 | 2/1994 | Delp . |
| 5,413,928 | 5/1995 | Weathers et al. . |

OTHER PUBLICATIONS

Vieitez, A.M., M.L. Vieitez and E. Vieitez, 1986. (Chestnut Castanea spp.). In: Biotechnology in Agriculture and Forestry, vol. 1: Trees I (Y.P.S. Bajaj ed.), Springer–Verlag, pp. 393–414.

Serres, R., Read, P., Hacket, W., et al. Rooting of American chestnut microcuttings. J. Environ. Hortic. 8:86–88; 1990.

Chevre, A.M., Gill, S.S., et al., In vitro vegetative multiplication of Chestnut. J. Hort. Science 58(1) 23–29, 1983.

Xing, Z., Satchwell, M.F., et al. Micropropagation of American Chestnut: Increasing Rooting Rate and Preventing Shoot–Tip Necrosis. In Vitro Cell. Dev. Biol. Plant 33:43–48, Jan. 1997.

Davis, T.D., Haissig, B.E. 1994. Biology of Adventitious Root Formation, Basic Life Sciences, vol. 62, pp. 249–251.

George, E.F., 1993. Plant Propagation by Tissue Culture, Part I, The Technology, pp. 470–471.

Nissen, S.J., Sutter, E.G., Stability of IAA and IBA in Nutrient Medium to Several Tissue Culture Procedures. HortScience 25(7):800–802, 1990.

Yassen, Y.M., Barringer, S., et al., Activated Charcoal in Tissue Culture: An Overview. Plant Growth Regulator Society of America, vol. 23, No. 4, pp. 206–212, 1995.

Wang, P.J., and Huang, L.C., In Virto, vol. 12, No. 3, pp. 260–262,1976, Beneficial Effects of Activated Charcoal on Plant Tissue and Organ Cultures.

*Primary Examiner*—Leon B. Lankford, Jr.
*Attorney, Agent, or Firm*—Shook, Hardy & Bacon L.L.P.

[57] ABSTRACT

A system for stimulating rooting of an in vitro tissue culture of a plant species includes a container supporting a composite comprising a first and second medium. The first medium is conducive to promoting rooting of the tissue culture. The second medium is formed of an opaque material which blocks the passage of light to first medium.

14 Claims, 1 Drawing Sheet

SYSTEM FOR PROPAGATING IN VITRO TISSUE CULTURES OF A PLANT SPECIES

This invention relates generally to a propagation system for in vitro tissue cultures or explants of various plant species, and more particularly, to a system that increases rooting response and produces functional root systems in such cultures or explants.

BACKGROUND OF THE INVENTION

The need to increase the rooting response of plant cultures is important when trying to produce identical copies of a mature plant. Mature plant cultures are generally difficult to propagate. However, it is necessary to use mature plant tissue to determine the characteristics or properties of progeny tissues. For example, it is not possible to determine whether a culture is blight resistant unless the culture is a mature plant. If the mature plant is resistant, then copies of the plant will also be resistant. Thus, it is desirable to have a method for growing tissue cultures from mature plants.

Scientists and industry have had a difficult time culturing certain types of plant tissue. Mature tissue samples do not develop into functioning plants when grown in a clear medium. The leaves are not formed properly, and the roots do not form properly, if at all. This difficulty may be due to the fact that the upper portion of a plant culture requires light while the lower portion requires darkness. In addition, certain substances which are required for growth and development of plant cultures are most effective in dark conditions. When these substances are exposed to light, which is often the case in conventional, in vitro, rooting systems, they break down. The break down of these substances prevents proper culture development.

Attempts have been made to create an in vitro environment that offered darkness to the lower portion of the culture and light to the upper portion of a culture. One prior conventional rooting system utilized charcoal in the rooting medium. Charcoal is added directly to the lower medium in an amount rendering the entire medium opaque. This represents an effective method for blocking light from the culture while allowing the upper or exposed portion of the explant to absorb light. However, several drawbacks exist in this type of system. For instance, charcoal in even minimal concentrations has been found to absorb growth regulators or auxins, such as Indole-3-Acetic Acid (IAA) and Indole-3-Butyric Acid (IBA). These auxins are essential for tissue growth as and development. In addition to absorbing these auxins, charcoal has been shown to absorb thiamine, nicotinic acid, pyridoxine, folic acid, iron chelate and zinc. Yet another problem experienced in the use of charcoal results from the lack of consistency of such systems due to the difficulty in regulating the amount of auxins absorbed by the charcoal. This problem makes it difficult to develop standard protocols.

Another problem encountered in the use of the conventional charcoal-bearing system is that the charcoal renders observation of the growth and development of tissue difficult or impossible. To ensure the best success rate for the cultures, it is important to remove them from the system as soon as the rooting system has matured sufficiently for transfer to a soil system. The charcoal saturated medium does not allow for such inspection, thus leaving to conjecture the timing for removal of the tissue from the system.

Another known rooting system that has been employed, specifically with the American Chestnut of the genus Castanea, involves a three-medium system. The system is used in the rooting of the American chestnut due to the traditionally low success rate experienced with other conventional methods. The three-medium system involves placing an explant in a first medium for 4–8 weeks, followed by placement in a second medium for 2 weeks, and finally placement in a third medium for 3 weeks. Unfortunately, this system does not have the best success rate. In addition, this system is time consuming, rendering the system impractical for commercial applications. Moreover, each transfer of the explant increases the chances that it will become contaminated.

BRIEF SUMMARY OF THE INVENTION

It is, therefore, a broad object of the present invention to provide a rooting system that increases rooting response and produces functional root systems in in vitro explants of various plant species.

In particular, it is an object of the invention to provide a system that blocks light from the rooting portion of the explant while allowing light to reach the upper portion of the explant. The amount of light which reaches the lower portion of the explant, as determined through testing of the best mode, is less than 1 $\mu mol \times meter^{-2} \times s^{-1}$.

Another object of the invention is to provide a rooting system that allows development of various tissues in an environment that will not damage auxins or require supplementation of auxin.

A further object of the invention is to provide a rooting system that allows for visual inspection of the lower portion of the tissue to increase the percentage of successful cultures.

Another object of the invention is to provide a rooting system that allows reproducibility.

A further object of the invention is to provide a rooting system that allows for a single environment throughout the early stages of development.

To accomplish these and other objects evident from the following description of the preferred embodiment of the invention, a culturing system is provided for stimulating rooting of an explant of a plant species. The system includes a composition comprising a first medium conducive to the growth and development of the explant and a second medium including an opaque material that blocks the passage of light to the first medium.

Additional objects, advantages, and novel features of the invention will be set forth in part in a description which follows, and in part will become apparent to those skilled in the art upon examination of the following, or may be learned by practice of the invention.

BRIEF DESCRIPTION OF THE DRAWING

The accompanying drawing forms a part of this specification and is to be read in conjunction therewith. Reference numerals are used in the drawing to indicate like parts disclosed below.

DETAILED DESCRIPTION OF THE INVENTION

Figure 1:
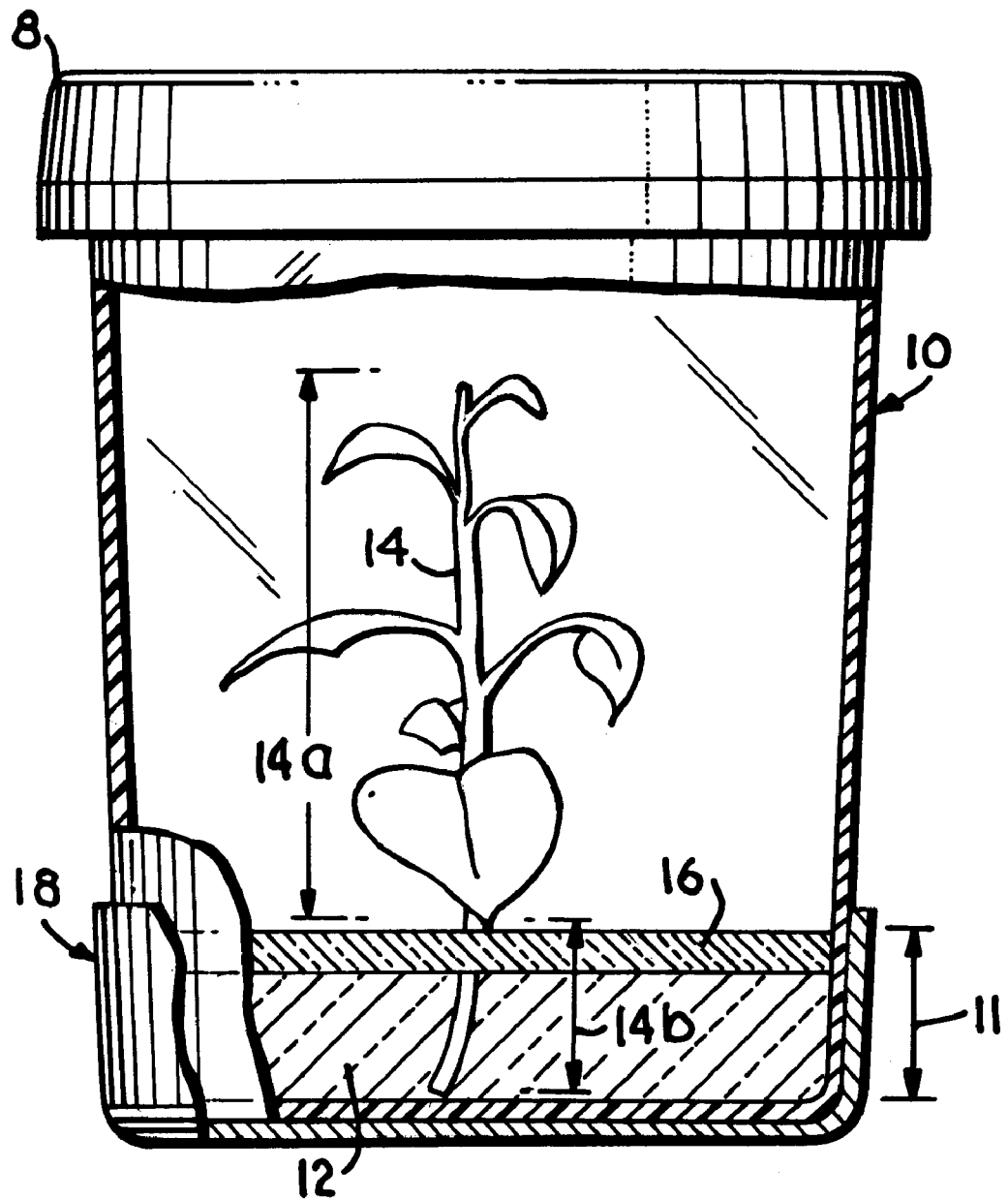
FIG. 1 is a cross section of a bilayer culturing system embodying the principles of this invention.

Referring to FIG. 1, a rooting system is shown for use in rooting in vitro explants of various plant species. The system broadly includes a cover 8, a container 10 defining the boundaries of the system, and a composite 11 comprising a first medium 12 and a second medium 16 disposed within the container 10. A tissue culture 14 is shown positioned in the composite between the first 12 and second medium 16. Tissue culture 14 has an upper region 14a and a lower region 14b. Lower region 14b is in the dark and upper region 14a is in the light. The container 10 and the composite 11 are sterile with the container 10 allowing for sterile growth conditions.

The container 10 is illustrated as a cup-shaped glass beaker or the like. A removable sleeve 18 of opaque material surrounds the container 10 to block light from reaching the first medium 12 contained therein. It is understood that the illustrated container is merely representative of any type of containing device or arrangement capable of supporting the composite 11 in the manner described herein, and the container 10 may be clear or opaque, depending on the application, and may be formed of glass, plastic, ceramic, or any other suitable material. In the preferred embodiment, the container is a clear plastic, 97 mm tall square with a length and width of 77 mm. Removable sleeve 18 is opaque and surrounds container 10 preventing light from reaching the lower region 14b of the culture 14. The sleeve 18 extends at least up to the second medium 16 thereby preventing light from reaching the lower region 14b of the tissue culture 14. The removable sleeve 18 may be formed of aluminum foil, paper, plastic, glass, metal, or any other substance that will prevent light from reaching the lower region 14b of the culture 14. Removable sleeve 18 is constructed of aluminum foil.

First medium 12 is substantially translucent. The first medium 12 comprises any substance or composition that is conducive to the growth of culture 14. In one embodiment, the first medium 12 is formed with McCown's woody plant basal salt mixture (WPM) containing 0.01 mg IBA/L. The preferred embodiment of first medium 12 comprises 1.15 g WPM, purchased from Sigma®, catalog #WPM M-6774, 2.61 g DKW/Juglans basal salt mixture (DKW), purchased from Sigma®, catalog #DKW D-6162, 100 mg myo-inositol, 0.75 mg nicotinic acid, 1.5 mg thiamine HCl, 2 mg glycine, 0.25 mg pyridoxine, 0.01 mg IBA, 0.2 mg 6-benzylaminopurine (BA), and 20 g sucrose. Bring these components to 1 liter and pH to 5.6 with 1 M KOH. Stir in 0.88 g of Gelrite® and 2.65 g of Agar. Heat the medium 12 until clear. Add the medium to the containers 10 and autoclave for 25–30 minutes.

Second medium 16 is an opaque matrix that substantially prevents light from passing through to first medium 12. The second medium can be made of plastic, glass, paper, Styrofoam, dirt, card board, filter paper, metal, or any substance that substantially prevents the passage of light. Even though it is preferred that the material used to form second medium 16 substantially block light, it is envisioned that the second medium 16 be of a nature to allow for the passage of varying amounts of light. Further, it is preferred that second medium is formed from a liquid that will solidify and conform to the shape of the container 10. Second medium 16 can be of varying thickness. The most preferred formulation of the second medium 16 is any ratio of the following: 100 ml of distilled deionized water, 0.88 g of Agar, and 2 g of powder activated (Norit Sg®) charcoal. With the most preferred embodiment being prepared by mixing 300 ml of distilled deionized water, 2.64 g Agar, and 6 g powder activated (Norit Sg®) charcoal from Manufacturing Chemistry Incorporated. After these components are mixed together, they are sterilized by autoclaving for 25–30 minutes. This sterilized mixture is then added to the hardened surface of the first medium to form a thin uniform light blocking layer. The preferred amount of blockage is the same amount as would be found in nature. The most preferred amount of the second media 16 to add is 5 to 7 ml when using the 97 by 77 by 77 mm clear plastic Magenta® GA-7 container. By varying the amounts of charcoal or the thickness of the second medium 16, varying amounts of light passing to first medium 12 may be allowed.

Culture 14 may be any living tissue. In one embodiment, culture 14 is a plant material from woody plant species that is recalcitrant to root. The culture 14 could be orchids such as Paphiopedilum. In the preferred embodiment, culture 14 is a tissue culture of a cross between *Castanea dentata* (Marsh) Borkh (American Chestnut) and *Castanea mollissima* Blume (Chinese Chestnut).

The culture 14 is added to the system by cutting a small slit in the second medium 16 with a sterile knife; the explant material is then inserted into the system.

The method for making the culturing system of the present invention includes providing a means for defining the boundaries of the container, forming in the container a composite comprising a first medium conducive to culture growth and a second medium which is substantially resistant to the passage of light, whereby the second medium prevents the passage of light to the first medium.

The rooting system of the present invention provides numerous advantages over prior art systems. For example, by employing a rooting system having a first medium that substantially blocks the passage of light to the lower layer, the system prevents damage to auxins in the system while at the same time reducing the amount of growth promoters that must be added to the system for increasing the rooting response of the plant.

Another advantage of the invention is that it allows for visual inspection to be made of the lower portion of the culture. By allowing visual inspection of the roots of the plant, the percentage of successful cultures can be increased relative to conventional systems, eliminating wasted time and resources.

The present invention also permits reproducibility of culture results by removing the presence of charcoal from the lower layer of the system carrying the auxins and growth promoters. The absence of the charcoal and the unpredictable absorption it causes are thus avoided, rendering the system particularly suitable for use in both laboratories and the commercial sector.

Another advantage of the invention is that those cultures which are inhibited by charcoal can now be grown in a system which allows for many different light combinations. It is not necessary to move the explant from medium to medium in order to obtain success with difficult-to-grow species, such as recalcitrant woody plant species.

From the foregoing, it will be seen that this invention is one well-adapted to attain all the ends and objects hereinabove set forth together with other advantages which are obvious and which are inherent to the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A culture system comprising:

a container;

a composite contained in said container and including a first medium having properties conducive to culture growth, and a second medium received on the surface of the first medium to form a light-inhibiting layer;

wherein said second medium comprises a mixture of charcoal, auger and water.

2. The system of claim 1 said container has an opening.

3. The system of claim 2 further comprising a cover disposed to selectively, substantially close said opening.

4. The system of claim 3 wherein said container is transparent.

5. The system of claim 4, further comprising a removable opaque sleeve adapted to surround said container.

6. The system of claim 1 wherein said second medium substantially blocks the passage of light to said first medium.

7. The system of claim 1 wherein said second medium allows for the insertion of a plant culture.

8. The system of claim 1 wherein said first medium is transparent.

9. A culture system comprising:

a container;

a composite contained in said container and including a first medium having properties conducive to culture growth, and a second medium received on the surface of the first medium to form a light-inhibiting layer; and a removable opaque sleeve adapted to surround said container.

10. A method of preparing a culture system comprising:

providing a container having an opening;

forming a first medium in said container, said first medium being conducive to culture growth;

applying a second medium to the surface of said first medium, said second medium inhibits the passage of light to said first medium; and placing a removable opaque sleeve around a lower region of said container.

11. The method of claim 10 further comprising the step of inserting a plant culture into said first medium.

12. The method of claim 10 further comprising the step of placing a cover over the opening in said container.

13. A system for stimulating rooting of an explant of a plant species comprising:

a lower layer formed of a first medium including at least one nutrient for promoting rooting of said explant;

an agar based upper layer received on the surface of said lower layer, said upper layer comprising agar and an opaque material; and a means for containing said lower layer and said upper layer.

14. The system of claim 13 wherein the opaque material is charcoal.

* * * * *